United States Patent
Pscherer et al.

(10) Patent No.: US 9,974,967 B2
(45) Date of Patent: May 22, 2018

(54) IMPLANTABLE ELECTROMEDICAL DEVICE

(71) Applicant: BIOTRONIK SE & Co. KG, Berlin (DE)

(72) Inventors: Norbert Pscherer, Fuerth (DE); Hermann Kalb, Erlangen (DE); Erich Haas, Flachslanden (DE); Sahika Seidler, Nuremberg (DE)

(73) Assignee: BIOTRONIK SE & Co. KG, Berlin (DE)

(*) Notice: Subject to any disclaimer, the term of this patent is extended or adjusted under 35 U.S.C. 154(b) by 0 days. days.

(21) Appl. No.: 15/062,856

(22) Filed: Mar. 7, 2016

(65) Prior Publication Data

US 2016/0271403 A1   Sep. 22, 2016

Related U.S. Application Data

(60) Provisional application No. 62/135,712, filed on Mar. 20, 2015.

(51) Int. Cl.
| | |
|---|---|
| *A61N 1/00* | (2006.01) |
| *A61N 1/375* | (2006.01) |
| *A61N 1/36* | (2006.01) |
| *A61N 1/362* | (2006.01) |
| *A61N 1/39* | (2006.01) |
| *B22F 3/10* | (2006.01) |

(Continued)

(52) U.S. Cl.
CPC ............ *A61N 1/3754* (2013.01); *A61N 1/36* (2013.01); *A61N 1/362* (2013.01); *A61N 1/3956* (2013.01); *B22F 3/10* (2013.01); *B22F 5/00* (2013.01); *B22F 7/06* (2013.01); *A61N 1/3756* (2013.01)

(58) Field of Classification Search
USPC .................................................. 607/56, 119
See application file for complete search history.

(56) References Cited

U.S. PATENT DOCUMENTS

| | | | |
|---|---|---|---|
| 2008/0209723 A1 | 9/2008 | Darley et al. | |
| 2010/0016909 A1* | 1/2010 | Gachiengo | ........... A61N 1/3752 607/4 |

(Continued)

FOREIGN PATENT DOCUMENTS

| | | |
|---|---|---|
| DE | 102009003958 | 7/2013 |
| EP | 1 820 534 | 8/2007 |

OTHER PUBLICATIONS

European Search Report and Annex to the European Search Report on European Patent Application No. EP 16 15 8393, dated Jul. 26, 2016 (10 pages).

*Primary Examiner* — Nicole F Johnson

(74) *Attorney, Agent, or Firm* — Buchanan Ingersoll & Rooney PC

(57) ABSTRACT

An implantable electromedical device, including a casing part accommodating an electronic or electric functional unit, an electrode disposed on the outside of the casing part or a line connection, and a feedthrough, which surrounds an orifice of the casing part and accommodates at least one metallic conductor element connecting the electrode or the line connection to the functional unit, and which has a metallic circumferential flange, wherein the feedthrough comprises a ceramic base body, around which the circumferential flange and in which the conductor element are directly shrunk in a positively and non-positively connecting manner.

11 Claims, 2 Drawing Sheets

(51) Int. Cl.
*B22F 5/00* (2006.01)
*B22F 7/06* (2006.01)

(56) References Cited

U.S. PATENT DOCUMENTS

| | | |
|---|---|---|
| 2010/0121438 A1* | 5/2010 | Jarvik .................. A61M 1/101 623/3.13 |
| 2011/0048770 A1 | 3/2011 | Reiterer et al. |
| 2011/0232961 A1 | 9/2011 | Teske |
| 2012/0194981 A1 | 8/2012 | Kempf et al. |
| 2012/0319319 A1 | 12/2012 | Parker et al. |

\* cited by examiner

IMPLANTABLE ELECTROMEDICAL DEVICE

CROSS-REFERENCE TO RELATED APPLICATIONS

This patent application claims the benefit of U.S. Provisional Patent Application No. 62/135,712, filed on Mar. 20, 2015, which is hereby incorporated by reference in its entirety.

TECHNICAL FIELD

The present invention relates to an implantable electromedical device, comprising a casing part accommodating an electronic or electric functional unit, an electrode disposed on the outside of the casing part or a line connection, and a feedthrough, which surrounds an orifice of the casing part and accommodates at least one metallic conductor element connecting the electrode or the line connection to the functional unit and which has a metallic circumferential flange.

BACKGROUND

Such devices have been widely used for quite some time, in particular, as cardiac pacemakers or implantable cardioverters (specifically defibrillators). However, they can also involve a less complex device, such as an electrode lead or sensor line or a cochlear implant.

The majority of implantable electromedical devices that are significant in practice are intended to deliver electric pulses to excitable body tissue via suitably positioned electrodes. So as to carry out this function, electronic/electric functional units are accommodated in the housing of the device for generating the pulses and for suitably controlling the pulse generation, and electrodes or connections for at least one electrode lead are provided directly on the outside of the device, in the distal end section of which the electrodes for transmitting the pulse to the tissue are accommodated. The electronic/electric functional units in the housing interior are to be connected to the outer electrodes or electrode line connections in a way that, under special conditions of the implanted state, ensures absolutely and permanently reliable function.

In particular, feedthroughs are known, the base and insulating body of which are essentially made of ceramic material or glass, wherein multi-layer or multi-piece designs using metals or metal oxides have also been developed and are used. Such known feedthroughs largely meet the demands placed on them.

However, the known feedthrough designs are relatively labor intensive and, thus, costly to produce. In particular, multiple work and process steps are required, complex joining of multiple individual components is necessary, as is pretreatment of the same in some instances (such as, for example, cleaning, surface pretreatment, creation of the solderability, etc.), and the processes must therefore also comprise multiple test steps.

A method for producing a feedthrough of a device is known from German Patent Publication No. DE 10 2009 003 958 B4, in which a metallic conductor is provided with an insulating casing (specifically made of an oxide of the conductor) and a flange is shrunk onto this insulated conductor by way of powdered metal injection molding, followed by cooling. It is also known from European Patent Publication No. EP 1 820 534 A2 to generate a surrounding flange around a feedthrough that otherwise is preassembled from multiple parts, using the powdered metal injection molding process. It is also known from United States Publication No. 2008/0209723 to shrink a ceramic component during the processing stage of the so-called brown body or green body onto a metallic conductive pin.

It is known from United States Publication No. 2012/0319319 to generate feedthroughs for hermetically sealed device housings by forming both an insulative body and a conductor passing through the same by way of a powder injection molding process.

The present invention is directed toward overcoming one or more of the above-mentioned problems.

SUMMARY

It is an object of the present invention to provide an improved implantable electromedical device, which is cost-effective to produce and highly reliable.

At least this object is achieved in terms of the device aspect by a device having the features of claim 1, and in terms of the method aspect by a method having the features of claim 10. Advantageous refinements of the inventive concept are the subject matter of the dependent claims.

The present invention is based on the idea of using metal injection molding ("MIM") technology for the metallic components (e.g., pin) and flange of a feedthrough to produce a feedthrough in one process step. The process allows both the flange located on the outside and the pin located on the inside to form a secure mechanical-chemical connection with the insulator during shrinking as a result of a particular geometry. The shrinkage behavior of the components used can be matched to each other for the joint sintering process by presintering (such as, for example, brown body) or by a certain composition of the molding powder (share of the binder). This also applies to the physicochemical contribution of the process to the creation of a secure connection of the individual parts.

At least in preferred embodiments, the described method offers one or more of the following advantages:
  High repeating accuracy+positioning accuracy.
  No separate joining process for the individual components required.
  No solder required.
  Cost-effective in high quantities.
  Low equipping complexity.
  Considerable reduction of the production aids.
  Fewer test and pretreatment steps (process steps) necessary.

In one embodiment of the present invention, the circumferential flange and the, or each, conductor element are designed as sintered parts formed of the same material by way of powdered metal injection molding. In principle, it is also possible to form the circumferential flange and the conductor elements of different materials, but using the aforementioned method in each case. However, this requires more complex process control and is therefore less preferred from the present point of view.

In an advantageous embodiment, a respective extension, which is thus disposed directly on a device-inner and a device-outer surface or on a cut-out of the ceramic base housing provided there, is provided on the, or each, conductor element. Even more specifically, extensions disposed on a device-inner and a device-outer surface or on a cut-out of the ceramic base housing provided there are additionally provided on the circumferential flange.

Pressing is carried out in the process by cooling the hot-formed parts, these being the circumferential flange and the conductor element, which results in the same contracting in the thickness direction of the ceramic base body, or in the circumferential flange contracting in the direction normal to the interface between the circumferential flange and the ceramic outer surface. In a further advantageous embodiment, the, or each, extension is designed to surround the inner circumference of the circumferential flange or the outer circumference of the, or each, conductor element in a ring- or disk-shaped manner. In this way, the respective interface is covered entirely by the ceramic base body and thus hermetically sealed, in particular, without additional aids.

In a further embodiment of the present invention, the ceramic base body is formed substantially of aluminum oxide ceramic; however, in principle, other technical ceramics can also be used. The circumferential flange and/or the, or each, conductor element are further preferably formed of titanium or a titanium alloy. However, in principle, it is also possible to use related metals, such as, for example, molybdenum, tantalum, tungsten, vanadium, zirconium or iridium, and alloys of the same, or nickel or palladium, or the alloys thereof.

From the method perspective, an expedient embodiment of the present invention comprises the following steps:
forming a ceramic base body;
providing a metal injection mold;
inserting the ceramic base body in the partially or fully presintered state into the metal injection mold;
injecting molding material into the metal injection mold to form the circumferential flange and the, or each, conductor element;
sintering/heat treating the metal injection mold with the material accommodated therein for debinding, outgassing and shrinking the material forming the circumferential flange and the, or each, conductor element; and
removing the feedthrough from the metal injection mold.

The method will typically also include the later step of connecting the feedthrough to the casing, in particular, by way of welding or bonding or shrink fitting the casing to the circumferential flange of the feedthrough. The specific manner of assembling the feedthrough depends, of course, on the type of the device in which it is used.

In a first important use of the present invention, the device is designed as an electrostimulation device, in particular, a cardiac pacemaker or cardioverter, wherein the casing part is designed as a device housing, and the electrode or the line connection is disposed on a header, which is separate from the device housing, and the feedthrough is disposed between the device housing and the header. A further important use is an electrode lead, wherein, in particular, the casing-outer section of the conductor element is designed as an electrode at the same time.

Further embodiments, features, aspects, objects, advantages, and possible applications of the present invention could be learned from the following description, in combination with the Figures, and the appended claims.

DESCRIPTION OF THE DRAWINGS

Advantages and functional characteristics of the present invention will additionally become apparent from the description of exemplary embodiments based on the Figures. In the drawings.

DETAILED DESCRIPTION

Figure 1:
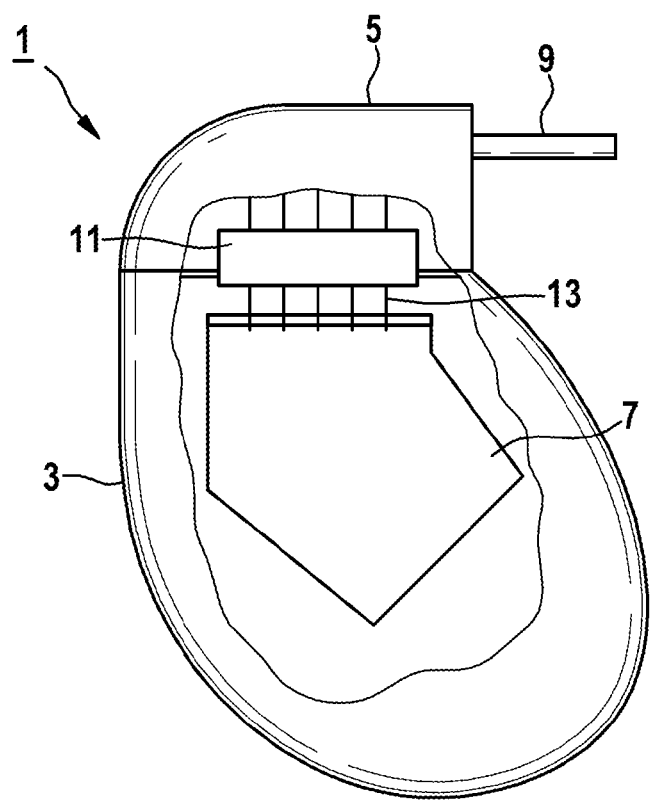
FIG. 1 shows a schematic, partially cut illustration of an implantable electromedical device.

FIG. 1 shows a cardiac pacemaker 1 comprising a pacemaker housing 3 and a header 5, in the interior of which a printed circuit board ("PCB") 7 is disposed, in addition to other electronic components, and to the line connection of which disposed in the header (not shown) an electrode lead 9 is connected. A feedthrough 11 provided between the device housing 3 and the header 5 comprises a plurality of terminal pins 13. At one end, the terminal pins 13 are placed through an appropriate borehole in the printed circuit board 7 and are soft-soldered thereto.

Figure 2:
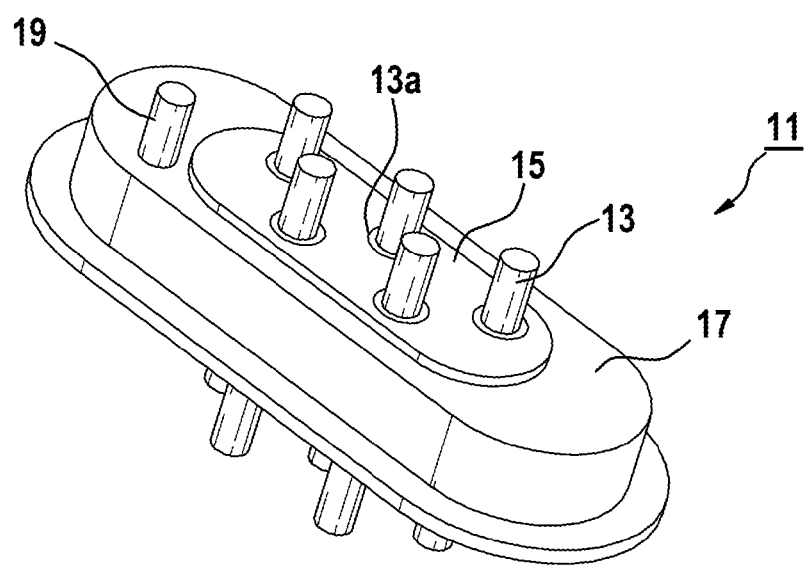
FIG. 2 shows a perspective illustration of an exemplary feedthrough of the device according to FIG. 1.
Figure 3:
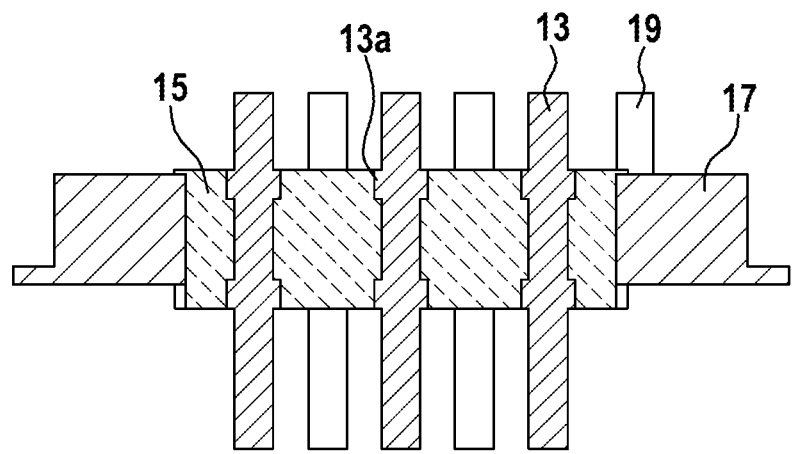
FIG. 3 shows a longitudinal sectional illustration of this exemplary feedthrough.

FIG. 2 shows a perspective illustration of one exemplary embodiment of the feedthrough 11, the components of which include a ceramic base body (insulator) 15 and a metallic circumferential flange 17, in addition to the terminal pins 13. A ground pin 19 is inserted into the circumferential flange 17. FIG. 3 shows the design of the same in a longitudinal sectional illustration.

The ceramic base body 15 is made of an aluminum oxide ceramic in this example; however, it can also be prefabricated from a zirconium oxide ceramic or another biocompatible ceramic material using conventional techniques, leaving open orifices that are adapted to the shape of the conductor elements (pins) 13. The circumferential flange 17 and the conductor elements (pins) 13 are molded on as part of or into the ceramic base body 15 in a hermetically sealed manner by way of a powdered metal injection molding ("MIM") process.

A non-positively sealed connection between the parts is created by shrinking the metal parts in this process. So as to be able to effectively utilize this effect for the pins 13, these are provided with annular thickened regions 13a in each case on the two surfaces of the ceramic base body 15. During the MIM process, these respective regions press against the neighboring inner annular surface of the ceramic base body 15 as a result of the longitudinal shrinkage of the pins 13 and connect thereto, both non-positively and by way of a physicochemical interface process. A similar process takes place on the inner circumference of the circumferential flange 17 with respect to the outer circumference of the ceramic base body 15.

The pins 13 and the circumferential flange 17 can be formed in a shared MIM process of the same material (such as, for example, a titanium alloy); however, it is also possible to produce them of different materials in consecutive processes. After debinding and sintering, the pins 13 can be completed with additional parts (sleeves or pads) or suitable coatings for the connection of further elements which are known per se to a person skilled in the art and, thus, are not illustrated in the Figures. The circumferential flange 17 can be connected in the customary manner to an orifice edge of the housing 3 (see FIG. 1) extending in corresponding fashion, such as by way of a laser welding process.

Figure 4:
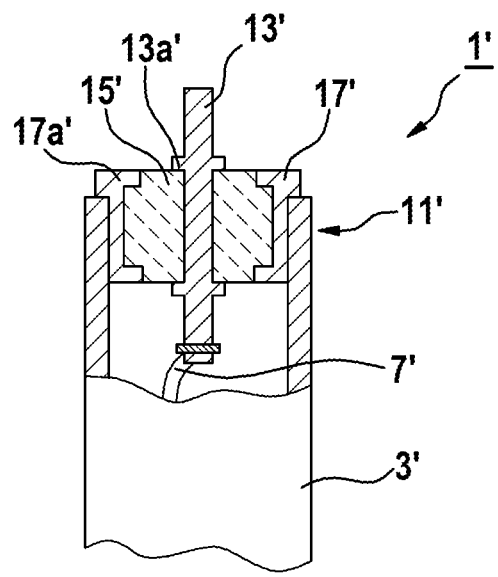
FIG. 4 shows a longitudinal sectional illustration of a further exemplary embodiment of the present invention.

FIG. 4 shows the distal end of an electrode lead 1' as a further exemplary embodiment, in which a feedthrough 11' forms the lead end. The feedthrough 11' comprises a single terminal pin 13', a ceramic base body 15', and a circumferential flange 17' and is shrink-fitted or glued into the free end of the lead sleeve 3'. The lead-outer section of the terminal pin 13', at the same time, serves as the outer functional element (electrode) of the electrode lead, and the proximal end thereof is connected to an electronic functional unit 7' in the conventional manner (such as, for example, by way of soft soldering). In the embodiment according to FIG. 4, both the terminal pin 13' and the circumferential flange 17' have annular thickened regions 13a' and 17a', respectively, at the opposing faces of the ceramic base body (insulator) 15', which shrink toward each other in the longitudinal direction during the MIM process in the manner described above and cause both the terminal pin 13' and the circumferential flange 17' to non-positively and sealingly connected to the insulator 15'.

The implementation of the present invention is not limited to these examples disclosed herein, but is likewise possible in a plurality of modifications, which are within the scope of standard practice in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable electromedical device, comprising:
   a casing part accommodating an electronic or electric functional unit;
   an electrode, disposed on the outside of the casing part, or a line connection; and
   a feedthrough, which surrounds an orifice of the casing part and accommodates at least one metallic conductor element connecting the electrode or the line connection to the functional unit and which has a metallic circumferential flange;
   wherein the feedthrough comprises an insulator base body, around which the circumferential flange and in which the conductor element are directly shrunk in a positively and non-positively connecting manner, and
   wherein the at least one metallic conductor element includes annular thickened regions at two opposing surfaces of the insulator base body, and wherein the annular thickened regions of the at least one metallic conductor element press against neighboring inner annular surfaces of the insulator base body as a result of longitudinal shrinkage of the at least one metallic conductor element and connect thereto.

2. The device according to claim 1, designed as an electrostimulation device including a cardiac pacemaker or cardioverter, wherein the casing part is designed as a device housing, and the electrode or the line connection is disposed on a header, which is separate from the device housing, and the feedthrough is disposed between the device housing and the header.

3. The device according to claim 1, designed as an electrode lead, wherein the casing-outer section of the conductor element at the same time forms an electrode.

4. The device according to claim 1, wherein the circumferential flange and the, or each, conductor element are designed as sintered parts formed of the same material by way of powdered metal injection molding.

5. The device according to claim 1, wherein at least one extension extending in a corresponding cut-out of the insulator base body is provided on the circumferential flange or the, or each, conductor element.

6. The device according to claim 5, wherein a respective extension, which is disposed directly on a device-inner and a device-outer surface or on a cut-out of the insulator base body provided there, is provided on the circumferential flange and on the, or each, conductor element so that the outer and inner extensions are pressed securely against the respective surface of the insulator base body.

7. The device according to claim 6, wherein the, or each, extension is designed to surround the inner circumference of the circumferential flange or the outer circumference of the or each conductor element in a ring- or disk-shaped manner.

8. A device according to claim 1, wherein the insulator base body is formed substantially of aluminum oxide ceramic.

9. The device according to claim 1, wherein the circumferential flange and/or the, or each, conductor element are formed of titanium or a titanium alloy.

10. A method for producing an implantable electromedical device according to claim 1, comprising the following steps:
    forming the ceramic base body;
    providing a metal injection mold;
    inserting the ceramic base body in the partially or fully presintered state into the metal injection mold;
    injecting molding material into the metal injection mold to form the circumferential flange and the, or each, conductor element;
    sintering/heat treating the metal injection mold with the material accommodated therein for debinding, outgassing and shrinking the material forming the circumferential flange and the or each conductor element; and
    removing the feedthrough from the metal injection mold.

11. The method according to claim 10, comprising a later step of connecting the feedthrough to the casing by way of welding or bonding or shrink fitting the casing to the circumferential flange of the feedthrough.

* * * * *